US00PP10347P

United States Patent [19]

van Andel

[11] Patent Number: Plant 10,347

[45] Date of Patent: Apr. 21, 1998

[54] ALSTROEMERIA PLANT VARIETY NAMED 'STAPRIMIL'

[75] Inventor: Jacob van Andel, Aalsmeer, Netherlands

[73] Assignee: Van Staaveren B.V., Aalsmeer, Netherlands

[21] Appl. No.: 716,498

[22] Filed: Sep. 16, 1996

[51] Int. Cl.[6] ..... A01H 5/00

[52] U.S. Cl. ..... Plt./87.1

[58] Field of Search ..... Plt./87.1

*Primary Examiner*—James R. Feyrer
*Assistant Examiner*—Kent L. Bell
*Attorney, Agent, or Firm*—Christie, Parker & Hale, LLP

[57] ABSTRACT

A new and distinct Alstroemeria plant variety producing flowers of good quality and attractive coloration, suitable for growing in pots.

1 Drawing Sheet

BACKGROUND OF THE INVENTION

The present invention relates to a new and distinct variety of Alstroemeria originated as a seedling by crossing as seed parent an unreleased, unpatented seedling identified as 87D1262-5 and as pollen parent an unreleased, unpatented seedling identified as 89G1041-01 from among my collection of Alstroemeria seedlings maintained under controlled conditions in a greenhouse at Van Staaveren B.V., Aalsmeer, The Netherlands, for developmental purposes. The varietal denomination of the new variety is 'Staprimil'.

The first act of asexual reproduction of 'Staprimil' was in Aalsmeer, The Netherlands, by propagation by dividing rootstocks. Asexual reproduction in Aalsmeer, The Netherlands, through successive generations has demonstrated that the combination of characteristics as herein disclosed for 'Staprimil' are firmly fixed and retained through successive generations of asexual reproduction.

'Staprimil' has not been observed under all possible environmental conditions. Phenotypic expression may vary with variations in environment such as temperature, light intensity, day length and growing and cultural conditions.

Comparison with 'Staprilan', application Ser. No. 08/716.499.

The new variety 'Staprimil' differs from the variety 'Staprilan' in the main flower color. 'Staprimil' is a lighter shade, near 5D than 'Staprilan', the main color of which is near 5C.

SUMMARY OF THE INVENTION

Flowers of the new variety of Alstromeria, 'Staprimil' are characterized by growth and flowers of unusual coloration, as described herein. The new variety is especially suitable for growing in pots.

DESCRIPTION OF ILLUSTRATIONS

The new variety of Alstroemeria hybrid is illustrated in the accompanying illustration, which shows typical growth and flower characteristics, with colors being as nearly true as is possible for illustrations of this type.

DETAILED DESCRIPTION OF THE NEW VARIETY

The following is a detailed description of the new cultivar of Alstroemeria hybrid as observed in a greenhouse in Aalsmeer, The Netherlands. Color designations indicated are in accordance with The Royal Horticultural Society Colour Chart by color plate designations.

Botanical classification:
- *Family.*—Amaryllidaceae.
- *Genus.*—Alstroemeria sp.
- *Commerical.*—Alstroemeria hybrid.

Origin: Seedling.

Plant

Form: Bush, pot-type.
Shape: Upright.
Height: About 30 to 40 cm.
Main stem or cane length: About 35 cm.
Growth: Vigorous, medium growth rate.
Strength: Strong.
Foliage:
- *Quantity.*—Abundant.
- *Number of leaves.*—About 20 to 25.
- *Size of leaf.*—Length: About 3 to 10 cm. Width: About 1 to 2 cm.
- *Shape of leaf.*—Elliptical.
- *Margin type.*—Minutely crimped.
- *Texture.*—Smooth.
- *Color.*—Upper side: Near 143A. Underside: Near 143B.
- *Rhizomes.*—Yes. Color: Near 155D. Size: About 10–15 cm.

Inflorescence—Flower/Floret

Blooming habit: Intermittent.
Blooms Profusely.
- *Spring.*—Yes.
- *Fall.*—Yes.
- *Has tendency to give few blooms in fall.*—No.

Size: Medium.
- *Diameter.*—About 5–6 cm.
- *Depth.*—About 4–5 cm.

Borne: Singly along simple racemes.
Shape or form:
- *When bloom first opens.*—Cup.
- *When bloom matures.*—Cup.

Petalage:
- *Number of petals.*—6.
- *Arrangement.*—Two concentric circles of 3 petals.
- *Form.*—Obovate.
- *Margin type.*—Straight.
- *Apex.*—Pointed.

*How long do petals stay on stem?*—About 3 weeks.
*Texture.*—Leathery.
*Appearance.*—Shiny.
*Color.*—Outer petal: Body near 5D, body tip near 63B; base near 62C; reverse side near 5D to 63B; 1–5 stripes, near 185A. *Inside petal:* Body near 12A; base near 12A; reverse side near 12A; about 20–30 stripes, near 185A.

Peduncle or flower stem:
*Length.*—About 2 to 3 cm.
*Color.*—Near 143A.
*Strength.*—Strong.
*Upright.*—Yes.

Discoloration after full bloom? Slightly, from near 5D to near 4D.
Is bloom affected by wet or hot weather? No.
Persistence (does flower hang on and dry?): No.
Disease resistance: Unknown.
Fragrance: None.
Lasting quality:
*On plant.*—About 3 weeks.
*As cut flower.*—About 14 days.

Bud

Size:
*Diameter.*—About 1 cm.
*Depth or length.*—About 2 cm.

Form or shape: Pear-shaped.
*Long.*—Yes.
*Pointed.*—No, ovoid.

Rate of opening: Fast.
Color of petals:
*When petals begin to unfurl.*—Near 59D.

Peduncle or flower stem:
*Length.*—About 2 to 3 cm.
*Hairy.*—No.
*Strength or character.*—Erect.
*Color.*—Near 143A.

Reproductive Organs

Stamen:
*Number.*—6.
*Arrangement.*—Around the style.

Anthers:
*Size.*—About 8 to 10 mm.
*Color.*—Near 152C.

Filaments:
*Length.*—About 5 cm.
*Color.*—Near 69A to 4C.

Pollen:
*Color.*—Near 152A.

Pistils:
*Number.*—1.

Styles:
*Length.*—About 4 to 5 cm.
*Color.*—Near 69A to 4C.

Stigmas:
*Color.*—Near 62A.

Fruit

Fertile: Yes.
Size: About 3 to 10 cm in length, and about 1 to 2 cm in width.
Texture: Smooth.
Margin: Straight.
Color:
*Topside.*—Near 143A.
Underside.—Near 143B.
Shape: Round.
Color at maturity: Near 164A.

I claim:

1. A new variety of Alstroemeria plant substantially as herein shown and described, suitable for growing in pots.

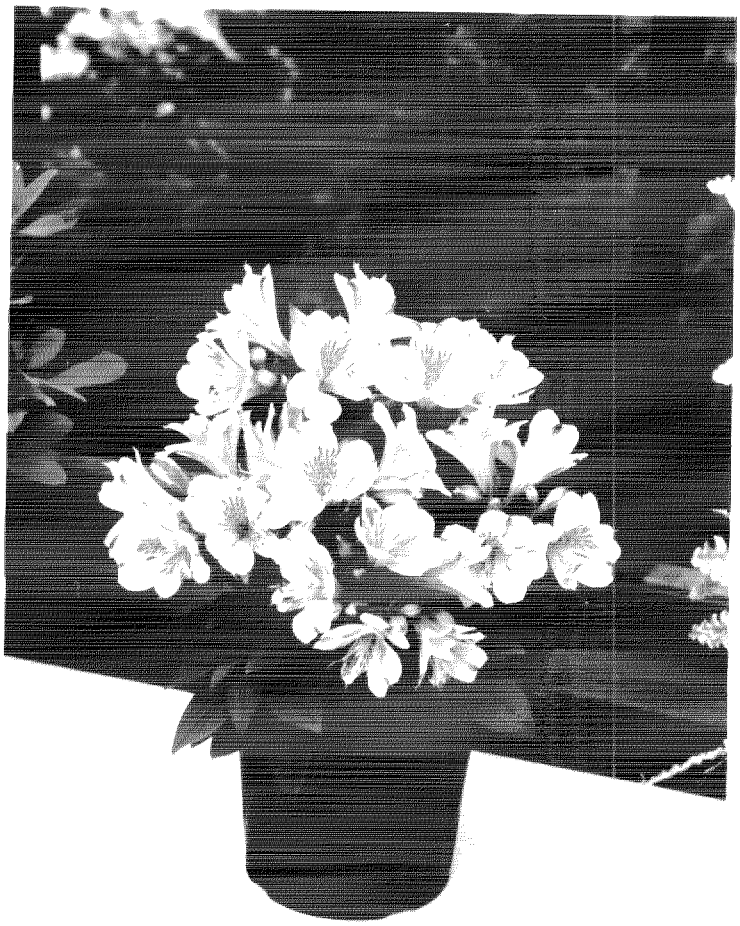

* * * * *